(12) United States Patent
Chang et al.

(10) Patent No.: US 6,323,022 B1
(45) Date of Patent: Nov. 27, 2001

(54) HIGHLY EFFICIENT CELL-CULTIVATING DEVICE

(75) Inventors: King-Ming Chang, Hsin-Chu; Long-Shuenn Jean, Chiayi; Yu-Tai Liu, Hsin-Chu; Chun-Chieh Chen, Tainan; Ken-Yuan Chang; Shu-Fang Chiang, both of Hsinchu, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/346,101

(22) Filed: Jul. 1, 1999

(51) Int. Cl.[7] ................................. C12M 1/36; C12M 3/00
(52) U.S. Cl. ........................... 435/286.5; 435/294.1; 435/297.2; 435/299.1
(58) Field of Search ................ 435/286.5, 286.6, 435/293.1, 299.1, 299.2, 297.2, 297.5, 305.1, 294.1, 284.1

(56) References Cited

U.S. PATENT DOCUMENTS 5,316,905 * 5/1994 Mori et al. .
5,766,949   6/1998 Liau et al. .
5,843,766 * 12/1998 Applegate et al. .

FOREIGN PATENT DOCUMENTS

| 4-158781 | * 6/1992 | (JP) | ................................. 435/294.1 |
| 1131899 | * 12/1984 | (SU) | ................................. 435/294.1 |
| WO 98/24880 | 6/1998 | (WO) . | |

OTHER PUBLICATIONS

Wilkins et al., *Development Of A Bilayered Living Skin Construct For Clinical Applications*, Biotech and Bioeng., vol. 43, pp 747–756 (1994).

* cited by examiner

*Primary Examiner*—William H. Beisner
(74) *Attorney, Agent, or Firm*—Darby Darby

(57) ABSTRACT

A cell-cultivating device includes a plurality of culture tanks and a driving device. The culture tanks communicate with each other and have culture medium inside. The driving device forces the culture medium to flow between the culture tanks so as to vertically oscillate medium levels in the culture tanks.

11 Claims, 8 Drawing Sheets

HIGHLY EFFICIENT CELL-CULTIVATING DEVICE

BACKGROUND OF THE INVENTION

1. Field of the Invention

The present invention relates in general to a highly efficient cell-cultivating device.

2. Description of the Related Art

The cell-cultivating industry is increasingly important due to the advances of biotechnology, and the corresponding market is continuously expanding. The characteristics of cells include: slow growth, easy damage by shearing forces and easy contamination by microbes, high cultivation cost, easy cultivation failure, and anchorage-dependence (for most cells). Due to these characteristics, the current cell-cultivating systems are not very successful. A general example of a cell-cultivating system is roller bottles. Each roller bottle can provide an area of only 850–1700 $cm^2$ for cultivating cells. Therefore, thousands of roller bottles are simultaneously taken care of in the factories, requiring a great deal of labor. Automation of the roller-bottle cell-cultivating system can save labor, but is expensive. Another example of a cell-cultivating systems is a stir tank. The tank has microcarriers inside for growing cells thereon. In this example, however, stirring culture medium and gassing cells considerably threaten growth of the cells. Furthermore, the operation conditions need to be changed when the dimensions of the stirring tank are enlarged (the enlargement is of three dimensions). Changes of the operation conditions greatly delay the product harvest. In addition, the cells tend to get contaminated when the stirring tank is enlarged. Another example of a cell-cultivating systems is hollow fibers, by which the cell density can be up to $10^8$. In this example, however, the reactor for cultivating cells is a plug-flow type. When the cell density increases to a predetermined level, the cells at the rear end of the reactor cannot obtain nutrition. To avoid such a situation, the reactor generally is not made large, which is the major disadvantage of the hollow fiber reactor. The device of the present invention adopts air/liquid circulation, and therefore is different from all the above-mentioned cell-cultivating systems.

U.S. Pat. No. 5,766,949 is most related to the present invention. It provides a system in which the culture medium oscillates up and down with respect to a substrate means provided in a cell-cultivating apparatus. Also, two storage tanks are provided for the culture medium circulating therebetween. A disadvantage of this system is that the culture medium in the storage tanks is not used to cultivate cells, and thus the use of the culture medium is not efficient. Furthermore, the use of a large substrate means it is necessary to increase the volumes of the storage tanks. Furthermore, two or more peristaltic pumps are simultaneously used to circulate the culture medium, so that control thereof is complicated.

Tissue engineering has been greatly developed in recent times. Artificial tissues such as artificial skins, artificial livers, artificial corneas and artificial blood vessels are produced outside human bodies. Because the number of elderly citizens and citizens suffering from burns or ulcers caused by diabetes are increasing from year to year, the market for artificial skins will be very large in the future. Thus far, the profits of selling artificial skins are very good, allowing companies not to consider reduction of cost by means of mass production. However, any commercial product in the end must face cost competitions. In addition, many kinds of tissue products, such as artificial blood vessels and artificial corneas are produced by processing layers of mammalian cells. Therefore, an apparatus for mass-producing layers of mammalian cells will be required in the future.

In "Biotechnology and Bioengineering, 1993", Leon M. Wilkins et al. disclose that cultivating skin cells requires a special environment. Specifically, simultaneously growing epithelial cells and endothelial cells to form an artificial skin of three-dimensional structure can be successful only at an air/liquid interface. It is common to use culture vessels to cultivate artificial skins. In this way, however, a culture vessel can produce only one piece of artificial skin. A great deal of labor and spaces are required to mass-produce artificial skins.

WO 98/24880 discloses a cell culture system in which a peelable polymer film is attached to a base of a flask. When a desired number of cells have been attached to the polymer film, the base is removed from the flask and the polymer film is peeled away from the base for applying to the patient. The system is advantageous because removing the artificial skin from the cell culture flask is convenient. However, a culture flask can only produce one piece of artificial skin. Therefore, such a method is not suitable for mass-production.

SUMMARY OF THE INVENTION

An object of the present invention is to provide a cell-cultivating device that solves the above-mentioned problems.

The cell-cultivating device of the present invention includes a plurality of culture tanks and a driving means. The culture tanks communicate with each other and have culture medium inside. The driving means forces the culture medium to flow between the culture tanks so as to vertically oscillate medium levels in the culture tanks.

In contrast to U.S. Pat. No. 5,766,949, the cell-cultivating device of the present invention operates without a buffer tank. The culture medium flows between the culture tanks and is therefore fully used. The driving means is an air compressor, a reversible peristaltic pump, an oil pressure cylinder or an air pressure cylinder, by which the cell-cultivating device is greatly simplified.

The substrate means contains carriers, which can be woven carriers, nonwoven carriers, plates, porous carriers made of ceramics or polymer, tissue engineering scaffold, or other common carriers. The woven carriers and nonwoven carriers are made of, for example, polymer which includes polyamide, polyester, polyurethane, polystyrene, polyaramid, fluorocarbon polymers, polyethylene, polyproplyene and polyvinyl alcohol. The plates are made of hard material such as polystyrene, polycarbonate, polyester, polypropylene, polyvinyl acetate, polyvinylidene chloride, polybutadiene, polyfluorocarbons and plates constructed by fibrous materials.

Furthermore, peelable polymer films are attached to both surfaces of each plate. Therefore, the present invention is superior to WO 598/24880, in which the polymer film can only be attached to one surface of the base. Furthermore, the plates are detachable from the culture tanks. This facilitates the packaging of the product and the application of the product to the patient. The plates are fixed by a supporting structure protruding from the inner walls of the culture tanks. The contact area between the plates and the culture tanks is small. In addition, the plates are taken away from the culture tanks by pulling rather than peeling. The action is not violent. Therefore, the product generally is complete and undamaged.

BRIEF DESCRIPTION OF THE DRAWINGS

The present invention can be more fully understood by reading the subsequent detailed description and examples with references made to the accompanying drawings, wherein.

DETAILED DESCRIPTION OF THE PREFERRED EMBODIMENT

Figure 1A:
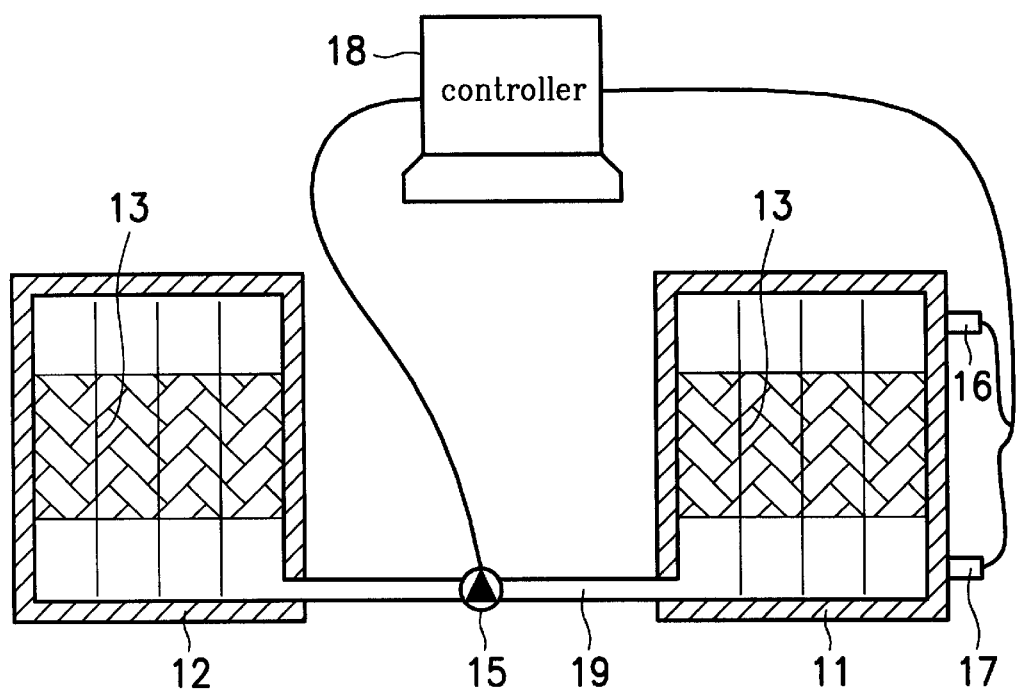
FIG. 1A shows a cell-cultivating device of a first embodiment of the present invention.

Referring to FIG. 1A, a cell-cultivating device of a first embodiment of the present invention includes two culture tanks 11, 12 with a pipe 19 connected therebetween. A peristaltic pump 15 is mounted on the pipe 19 to draw culture medium from the tank 11 to the tank 12 or from the tank 12 to the tank 11. Reference number 13 represents substrate means to which growing cells attach.

In operation, the peristaltic pump 15 draws culture medium from the tank 11 to the tank 12 so that the medium level in the tank 11 goes down and the medium level in the tank 12 goes up. When the medium level in the tank 11 goes down to a sensor 17, a signal is sent to a controller 18 for changing the operation of the peristaltic pump 15. Thus, the peristaltic pump 15 draws culture medium from the tank 12 to the tank 11 so that the medium level in the tank 12 goes down and the medium level in the tank 11 goes up. When the medium level in the tank 11 goes up to another sensor 16, another signal is sent to the controller 18 for changing back the operation of the peristaltic pump 15. Thus, the culture medium in the tanks 11, 12 is oscillated up and down to create an air/liquid environment suitable for the growth of skin cells.

In this embodiment, the peristaltic pump 15 forces the culture medium to flow between the two culture tanks 11, 12. The culture medium is always in use. Also, the two culture tanks 11, 12 are simultaneously used. Therefore, the production amount is large.

Figure 1B:
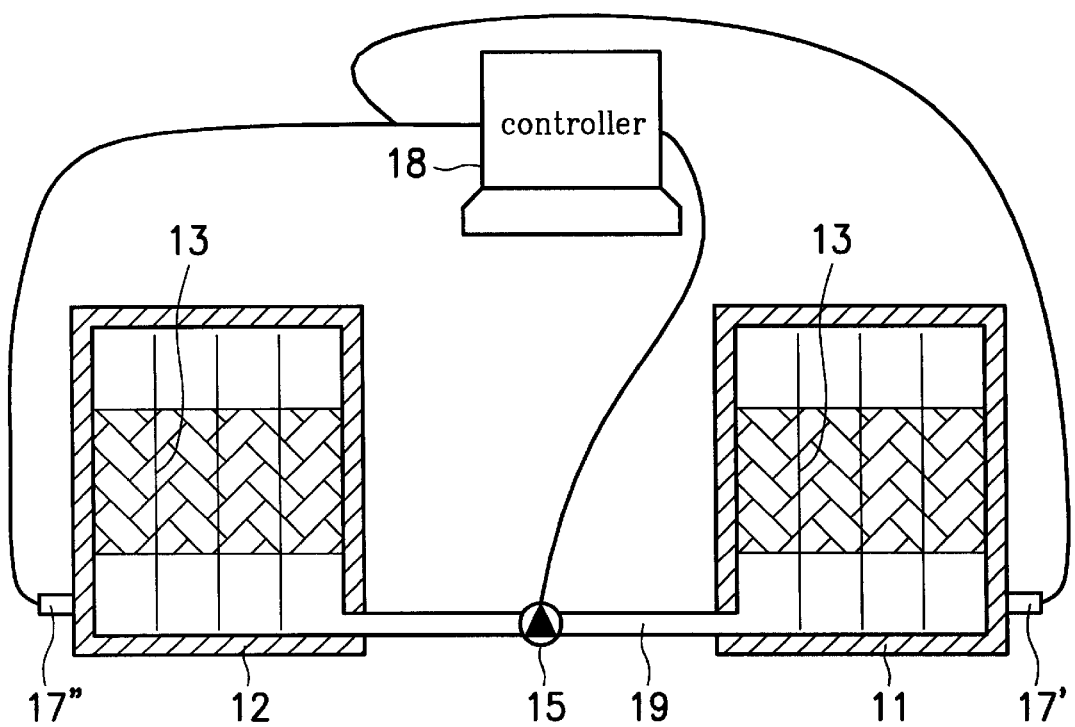
FIG. 1B shows a modified cell-cultivating device of the first embodiment of the present invention.
Figure 1C:
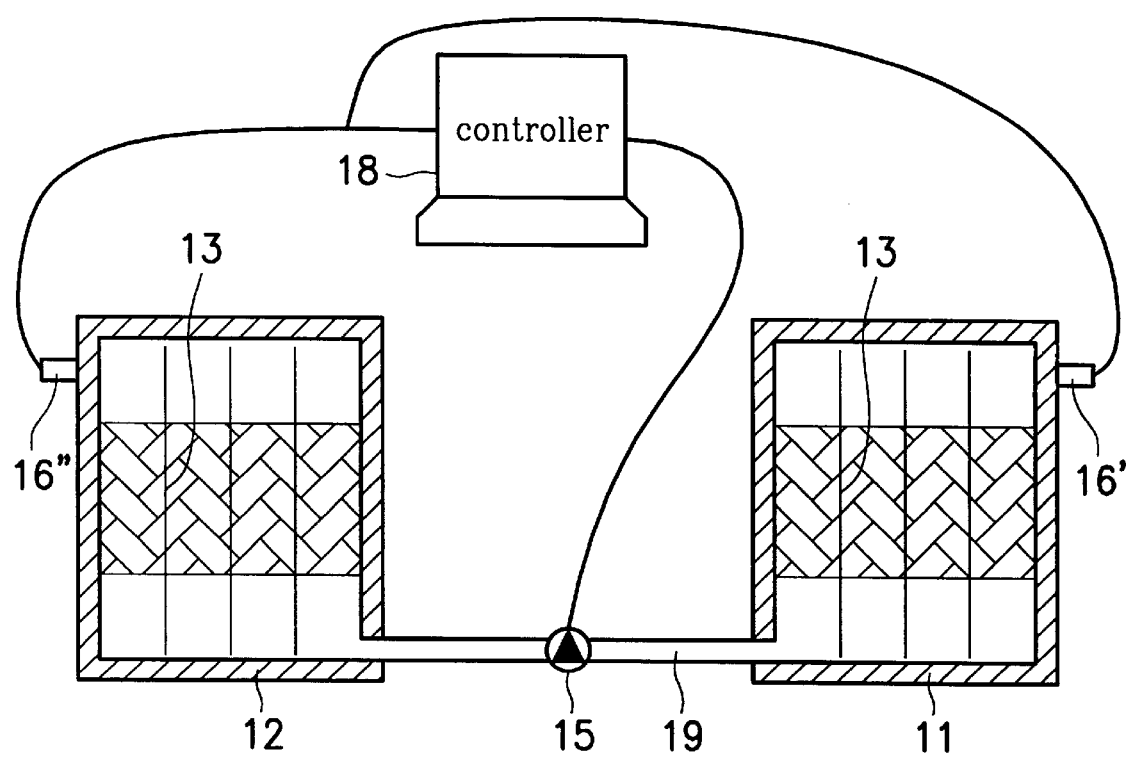
FIG. 1C shows another modified cell-cultivating device of the first embodiment of the present invention.

The first embodiment can be modified as shown in FIG. 1B, wherein sensors 17', 17" are provided on the bottoms of the culture tanks 11, 12. When the medium level in the tank 11 goes down to the sensor 17', a signal is sent to the controller 18 for changing the operation of the peristaltic pump 15. The peristaltic pump 15 draws culture medium from the tank 12 to the tank 11. Then, the medium level in the tank 11 goes up and the medium level in the tank 12 goes down. When the medium level in the tank 12 goes down to the sensor 17", a signal is sent to the controller 18 by the sensor 17" for changing the operation of the peristaltic pump 15 back. Alternatively, the first embodiment can be modified as shown in FIG. 1C, wherein sensors 16', 16" are provided on the tops of the culture tanks 11, 12. The operations of the peristaltic pump 15 are changed when the medium levels go up to either of the sensors 16', 16".

Figure 2A:
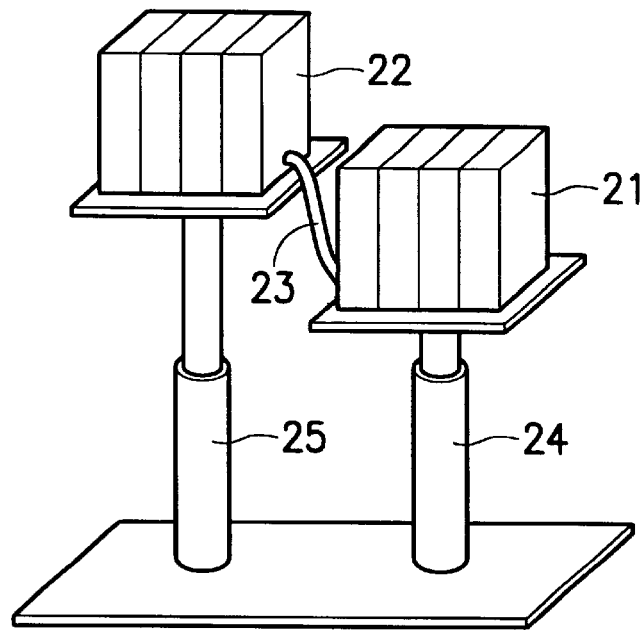
FIG. 2A shows a cell-cultivating device of a second embodiment of the present invention.

Now referring to FIG. 2A, the cell-cultivating device of a second embodiment of the present invention includes two culture tanks 21, 22 with a pipe 23 connected therebetween. Driving devices such as oil pressure cylinders or air pressure cylinders 24, 25 are mounted on the bottoms of the tanks 21, 22 for vertically moving the tanks 21, 22 in opposite directions. The tank 21 goes up when the tank 22 goes down. On the other hand, the tank 21 goes down when the tank 22 goes up. Based on the principle of the communicating pipe, the culture medium reciprocates between the two tanks 21, 22 so that the medium levels in the tanks 21, 22 are vertically oscillated. Alternatively, the medium levels in the tanks 21, 22 are vertically oscillated by moving one tank and fixing the other tank.

Figure 2B:
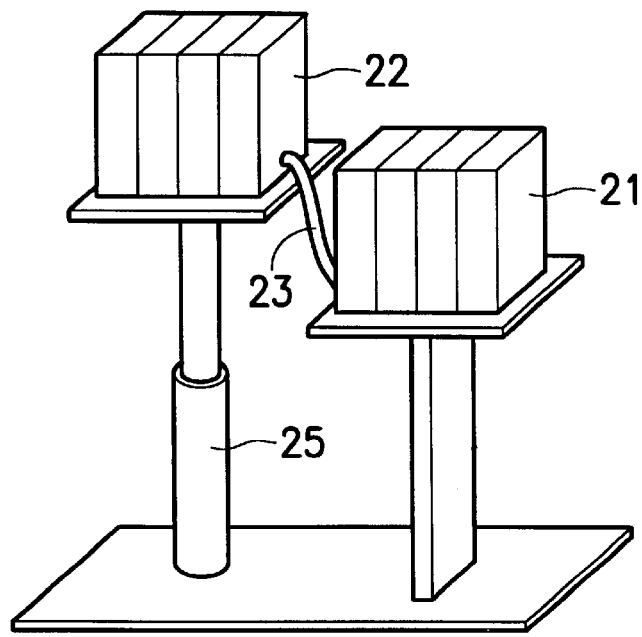
FIG. 2B shows a modified cell-cultivating device of the second embodiment of the present invention.

The second embodiment can be modified as shown in FIG. 2B, wherein the tank 21 is stationary while the tank 22 is vertically moved.

Figure 2C:
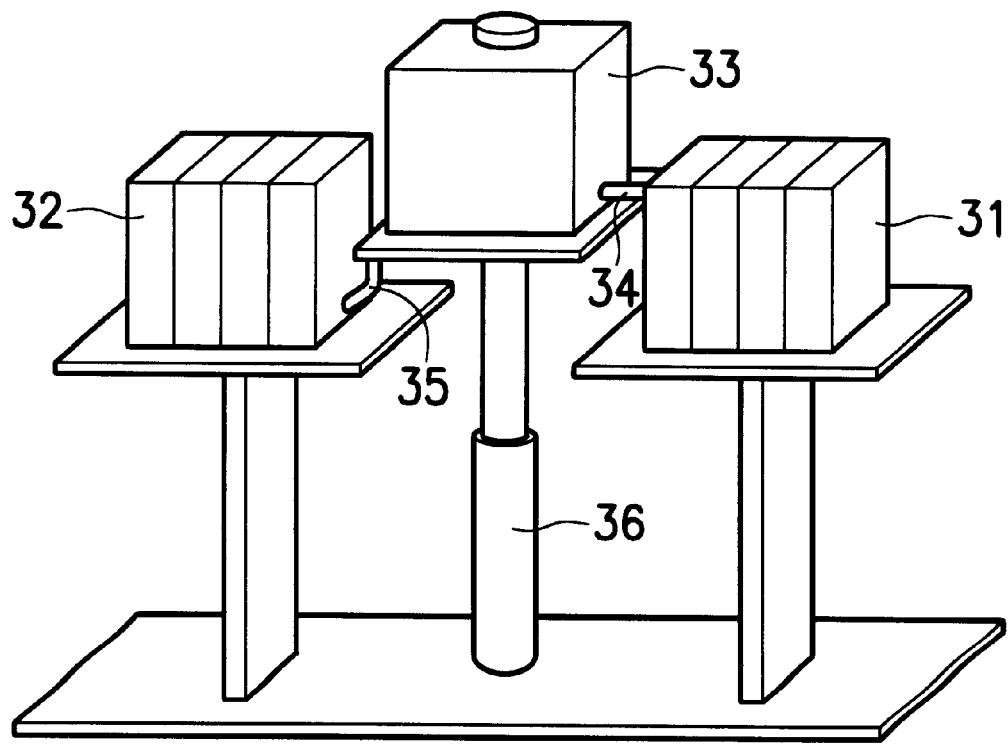
FIG. 2C shows another modified cell-cultivating device of the second embodiment of the present invention.

The second embodiment can be further modified as shown in FIG. 2C, wherein a buffer tank 33 is provided between the two tanks 31, 32. Reference numbers 34, 35 represent pipes. The culture tanks 31, 32 are stationary, while the buffer tank 33 is vertically moved by a driving device 36. By this arrangement, the medium levels in the tanks 31, 32 are vertically oscillated.

Figure 3:
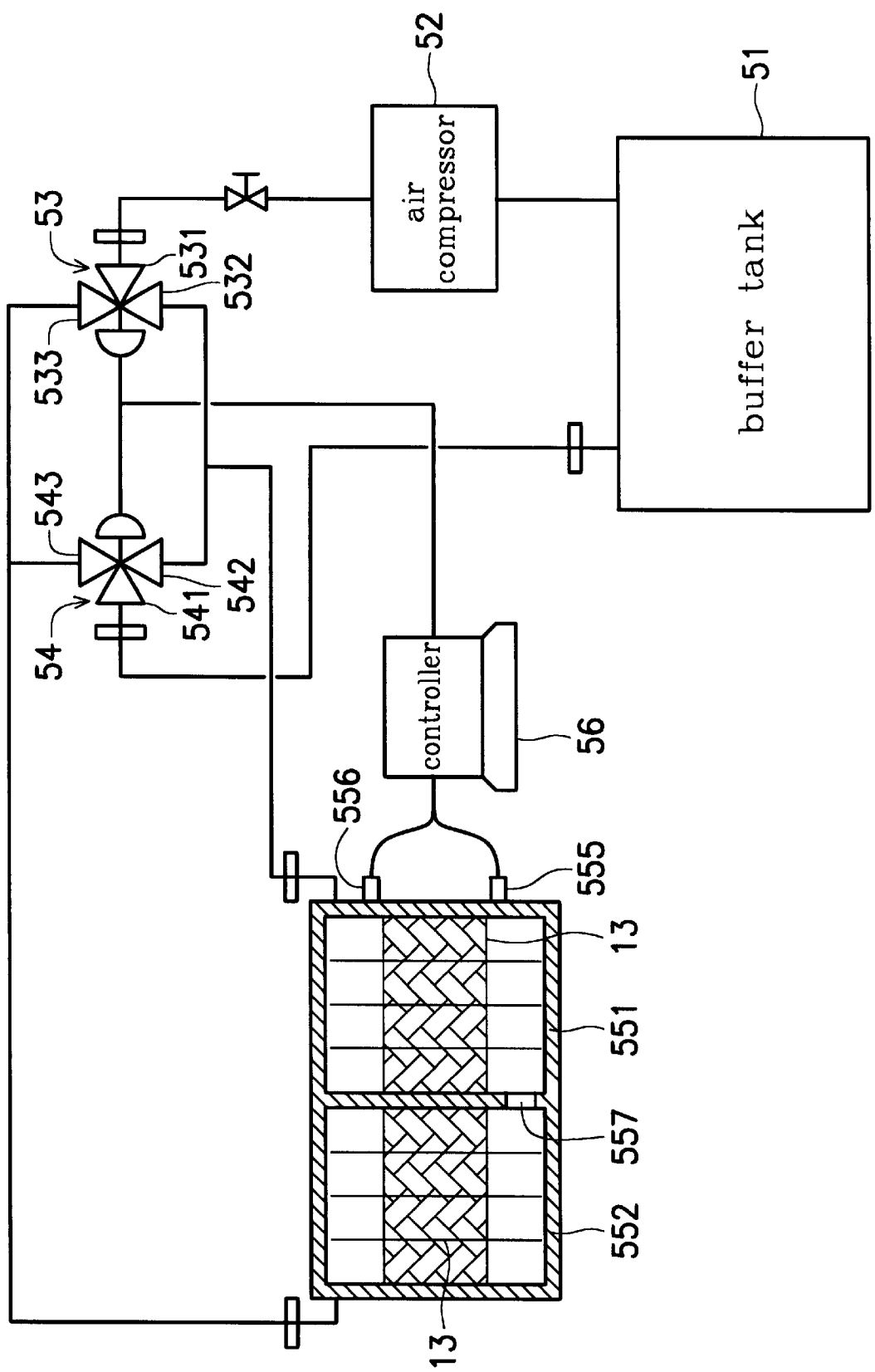
FIG. 3 shows a cell-cultivating device of a third embodiment of the present invention.

Referring to FIG. 3, the cell-cultivating device of a third embodiment of the present invention includes two culture tanks 21, 22 which communicate with each other by virtue of a hole 557 provided on their bottoms. Reference number 13 represents substrate means. In operation, the valve ports 531, 532 of the solenoid valve 53 are open and the valve port 533 is closed. Also, the valve ports 541, 543 of the solenoid valve port 54 are open and the valve port 542 is closed. Air in a buffer tank 51 is pushed into the culture tank 551 by an air compressor 52. Thus, the medium level in the culture tank 551 goes down by air pressure. Because the bottoms of the two culture tanks 551, 552 communicate with each other, the medium level in the culture tank 552 goes up when the medium level in the culture tank 551 goes down. Then, air on the top of the culture tank 552 is pushed into the buffer tank 51.

Sensors 556, 555 are provided on the top and bottom of the culture tank 551. When the medium level in the culture tank 551 goes down to the sensor 555, a signal is sent to a controller 56 by the sensor 555. Then, the controller 56 changes the open/closed status of the solenoid valves 53, 54. Specifically, the valve port 533 of the solenoid valve 53 is opened, the valve port 532 is closed, and the valve port 531 is still open without change. Also, the valve port 542 of the solenoid valve 54 is opened, the valve port 543 is closed, and the valve port 541 is still open without change. Then, air in the buffer tank 51 is pushed into the culture tank 552 through the solenoid valve 53 so that the medium level in the culture tank 552 goes down. Meanwhile, the medium level in the culture tank 551 goes up until the top sensor 556 detects the medium level. Then, a signal is sent to the controller 56 by the sensor 556 so as to change the open/closed status of the solenoid valves 53, 54. By repeating such an operation, the medium levels in the culture tanks 551, 552 are vertically oscillated.

It is understood that the sensors in this embodiment can be mounted, similar to the second embodiment, on the bottoms of the culture tanks 551, 552 or the tops of the culture tanks 551, 552 to vertically oscillate the culture medium therein.

Figure 4:
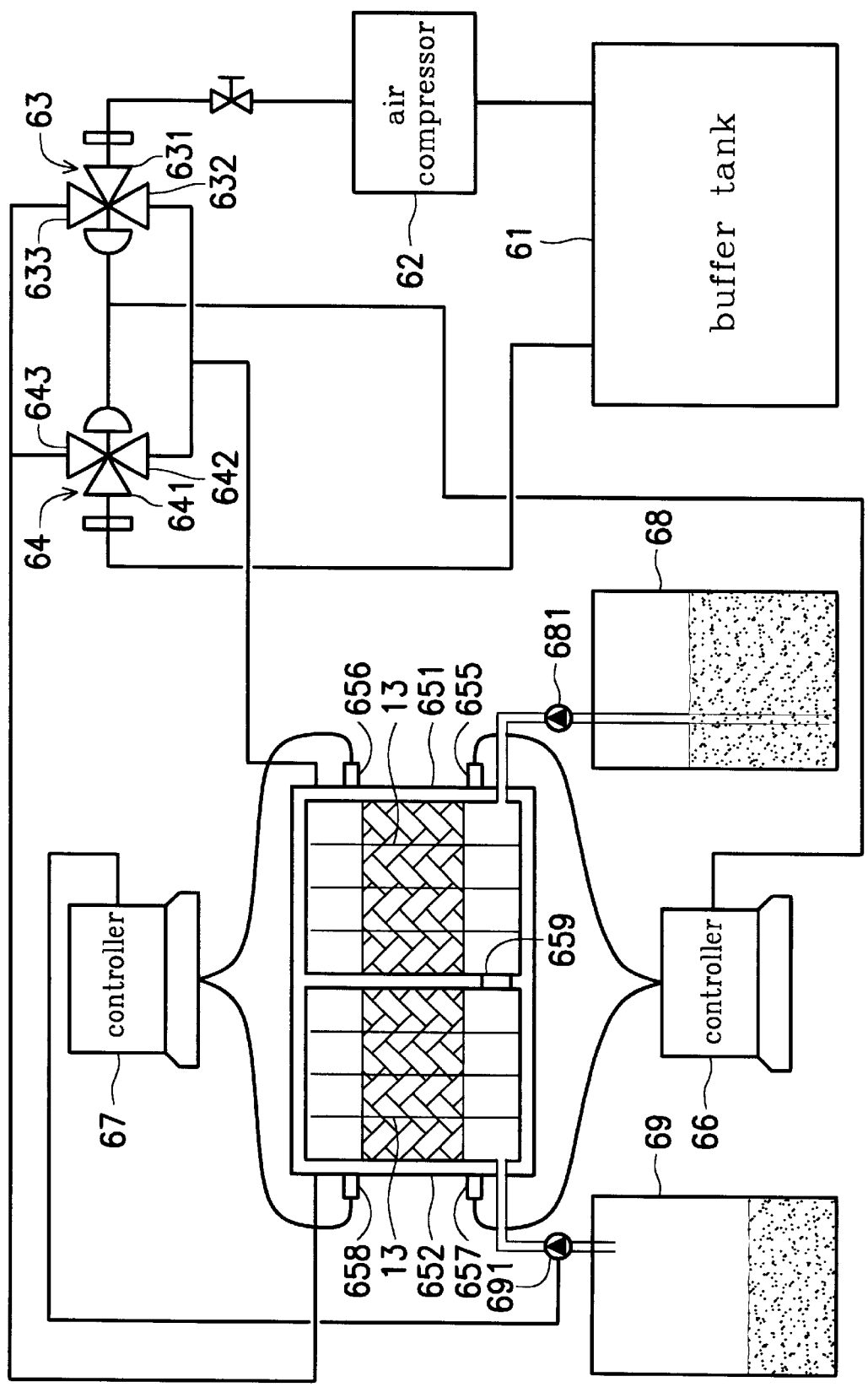
FIG. 4 shows a cell-cultivating device of a fourth embodiment of the present invention.

Referring to FIG. 4, the cell-cultivating device of a fourth embodiment of the present invention also includes two culture tanks 651, 652 which communicate with each other by virtue of a hole 659 provided on their bottoms. Reference number 13 represents substrate means. Two sensors 656, 658 are provided on the tops of the culture tanks 651, 652, while another two sensors 655, 657 are provided on the bottoms. The top sensors 656, 658 are connected to a controller 67 for controlling the operations of peristaltic pumps 681, 691. The bottom sensors 655, 657 are connected to another controller 66 for controlling the operations of solenoid valves 63, 64. The details are described as follows:

(1) In operation, valve ports 631, 632 of the solenoid valve 63 are open and the other valve port 633 of the solenoid valve 63 is closed. Also, valve ports 641, 643 of the solenoid valve 64 are open and the other valve port 642 is closed. Air in a buffer tank 61 is pushed into the culture tank 651 by an air compressor 62. Thus, the medium level in the culture tank 651 goes down by air pressure. Because the bottoms of the two culture tanks 651, 652 communicate with each other, the medium level in the culture tank 652 goes up when the medium level in the culture tank 651 goes down. Then, air on the top of the culture tank 652 is pushed into the buffer tank 51. When the medium level in the culture tank 651 goes down to the sensor 655, a signal is sent to a controller 66 by the sensor 655. Then, the controller 66 changes the open/closed status of the solenoid valves 63, 64. Specifically, the valve port 633 of the solenoid valve 63 is opened, the valve port 632 is closed, and the valve port 631 is still open without change. Also, the valve port 642 of the solenoid valve 64 is opened, the valve port 643 is closed, and the valve port 641 is still open without change. Then, air in the buffer tank 61 is pushed into the culture tank 652 through the solenoid valve 63 so that the medium level in the culture tank 652 goes down. Meanwhile, the medium level in the culture tank 651 goes up until the bottom sensor 652 detects the medium level. Then, a signal is sent to the controller 66 by the sensor 652 so as to change the open/closed status of the solenoid valves 63, 64. By repeating such an operation, the medium levels in the culture tanks 651, 652 are vertically oscillated.

(2) The growth of the cells attached onto the substrate means 13 reduces the nutrition of the culture medium. Therefore, the culture medium in the culture tanks 651, 652 is necessarily replaced in order to provide the growing cells with sufficient nutrition. At the beginning, the peristaltic pump 691 does not operate. Another peristaltic pump 681 operates to draw fresh culture medium from the storage tank 68 to the culture tanks 651, 652. Thus, the amount of the culture medium in the culture tanks 651, 652 increases. When the medium level goes up to the sensor 656 or 658, a signal is sent to the controller 67. Then, a peristaltic pump 691 is actuated by the controller 67 to draw the culture medium from the culture tanks 651, 652 to another storage tank 69. By this way, the culture medium in the culture tanks 651, 652 is replaced.

Figure 5A:
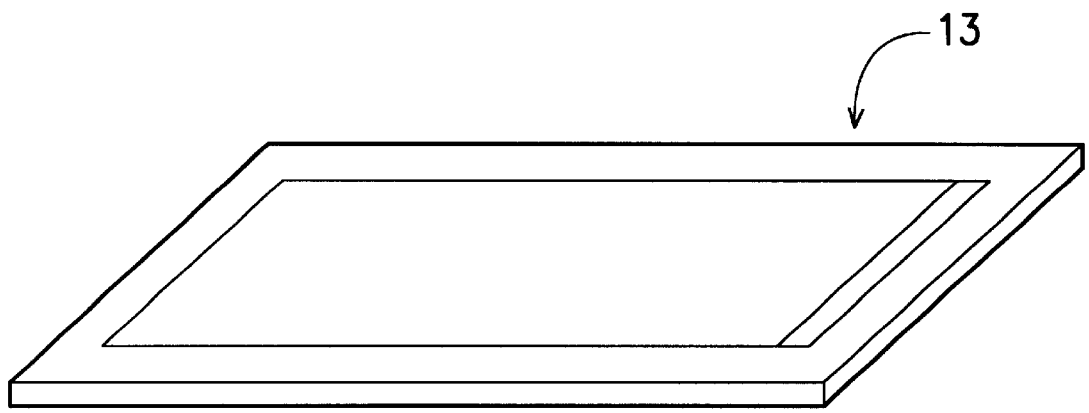
FIG. 5A is a perspective diagram of a substrate means of the present invention.
Figure 5B:
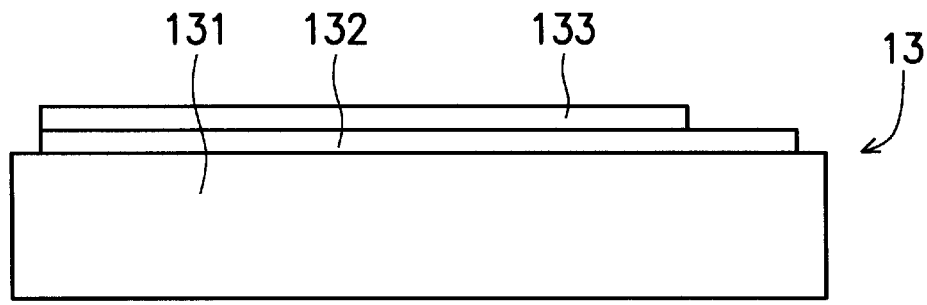
FIG. 5B is a front view of the substrate means shown in FIG. 5A.

Referring to FIGS. 5A and 5B, each of the substrate means 13 mentioned in the above four embodiments include a plate (or substrate object) 131, a first film 132 and a second film 133. The plate 131 is made of hard material such as polystyrene, polycarbonate, polyester, polypropylene, polyvinyl acetate, polyvinylidene chloride, polybutadiene, polyfluorocarbons and plates constructed by fibrous materials.

Furthermore, the plate 131 is detachable from the culture tanks. Three edges of the plate 131 are fixed by supporting a structure protruding from the inner walls of the culture tanks. The other edge of the plate 131 is provided with a handle so that the user can use prongs or other tools to take the substrate means out of the culture tanks.

The first and second films 132, 133 adhere to the plate 131 but are peelable from the plate 131. Specifically, a surface of the first film 132 adheres to the plate 131 while a surface of the second film 133 adheres to the other surface of the first film 132. The other surface of the second film 133 is used for growing epithelial cells thereon. The first film 132 is detachable from the plate 131. Also, the second film 133 is detachable from the first film 132. The first and second films 132, 133 are nonwoven sheets, woven sheets, polymer films or casting films, wherein the polymer films are made of hydrophilic polyurethane, polyester, polypropylene, polyvinyl acetate blends, polyvinylidene chloride, polystyrene, polybutadiene, polyfluorocarbons, collagen or their copolymer.

In conclusion, the present invention utilizes a plurality of culture tanks communicating with each other and a driving device for forcing culture medium to flow between the culture tanks. The culture medium is fully used. In addition, the production greatly increases because the culture tanks are simultaneously used.

Figure 6:
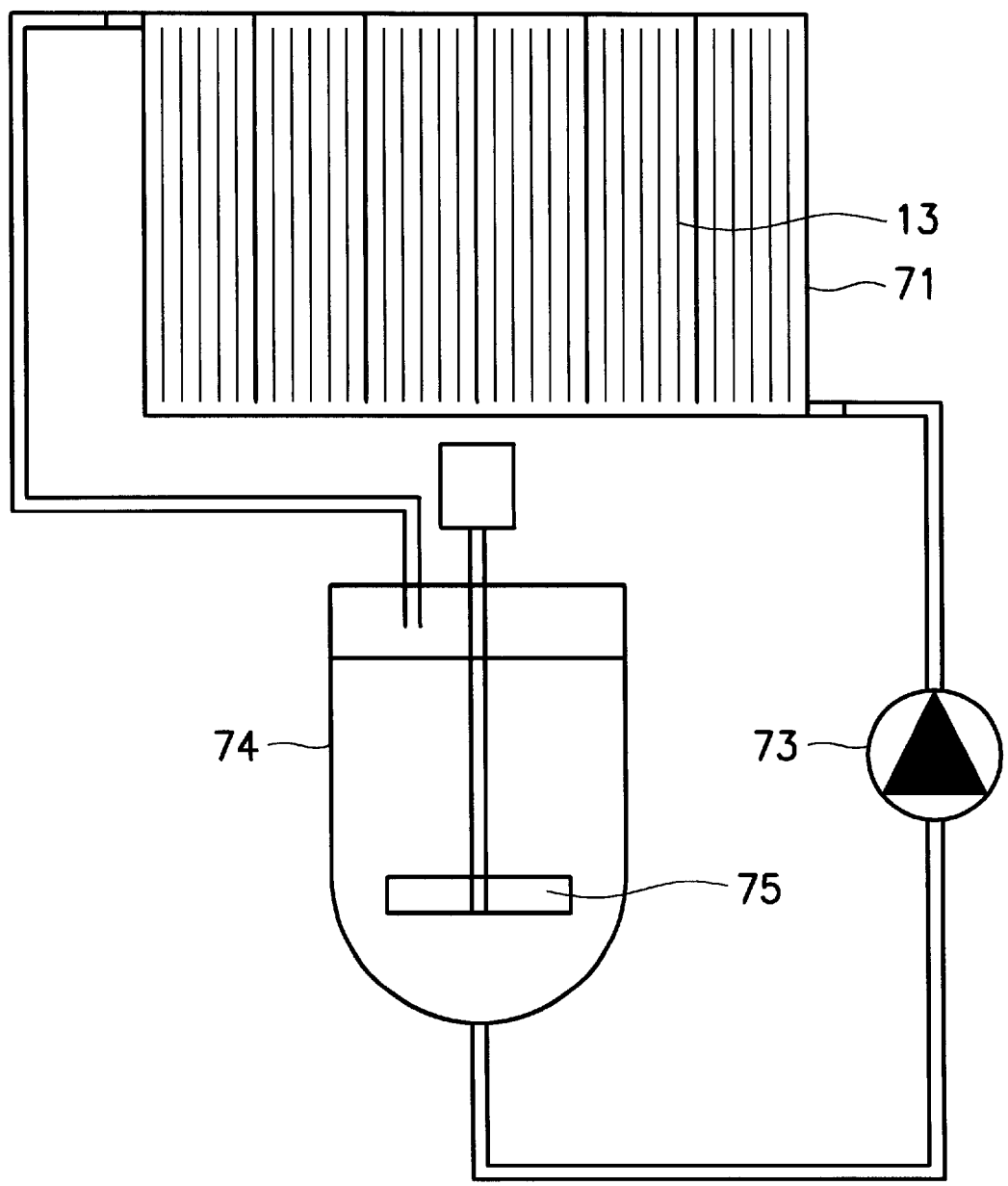
FIG. 6 shows a cell-cultivating device of a fifth embodiment of the present invention.

If it is intended to cultivate artificial skins of two-dimensional structure, such as endothelial cells, fibroblasts and keratinocytes, then another cell-cultivating device besides the above-mentioned cell-cultivating device can be used. Referring to FIG. 6, a cell-cultivating device of a fifth embodiment of the present invention includes a culture tank 71 and a buffer tank 74. The culture tank 71 has above-mentioned substrate means 13 inside for growing cells thereon. In operation, the culture medium is stirred by a stirrer 75 so that oxygen is fully dissolved in the culture medium. Then, the culture medium is drawn into the culture tank 71 by a peristaltic pump 73 to provide growing cells with nutrition and oxygen. Then, the used culture medium is drawn back to the buffer tank 74.

While the invention has been described by way of example and in terms of the preferred embodiment, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A cell-cultivating device comprising:
   a culture tank having culture medium therein;
   a tissue engineering scaffold in the culture tank, wherein the tissue engineering scaffold includes at least one substrate object, and at least one of said substrate objects having polymer films attached thereto, wherein at least one substrate object is a plate, said plate having a handle at its edge and comprising polystyrene, polycarbonate, polyester, polypropylene, polyvinyl acetate, polyvinylidene chloride, polybutadiene, polyfluorocarbons or fibrous materials
   a buffer tank; and
   a driving means for circulating the culture medium between the culture tank and the buffer tank.

2. A cell-cultivating device comprising:
   a plurality of culture tanks having a culture medium therein, wherein the plurality of culture tanks includes a first culture tank and a second culture tank;

a pipe connected between the plurality of culture tanks to permit communication between the plurality of culture tanks;

a peristaltic pump mounted on the pipe for forcing the culture medium to flow between the plurality of culture tanks so as to oscillate medium levels in the plurality of culture tanks;

a first sensor mounted near the top and a second sensor mounted near the bottom of the first culture tank;

a controller for receiving signals from the first and second sensors and actuating the peristaltic pump to draw the culture medium from the first culture tank to the second culture tank when a signal from the first sensor is received and actuating the peristaltic pump to draw the culture medium from the second culture tank to the first culture tank when a signal from the second sensor is received.

3. A cell-cultivating device comprising:

a plurality of culture tanks having culture medium therein, wherein the plurality of culture tanks includes a first culture tank and a second culture tank;

a pipe connected between the plurality of culture tanks to permit communication between the plurality of culture tanks;

a peristaltic pump mounted on the pipe for forcing the culture medium to flow between the plurality of culture tanks so as to oscillate medium levels in the plurality of culture tanks;

a first sensor mounted near the bottom of the first culture tank;

a second sensor mounted near the bottom of the second culture tank; and a controller for receiving signals from the first and second sensors and actuating the peristaltic pump to draw the culture medium from the second culture tank to the first culture tank when a signal from the first sensor is received and actuating the peristaltic pump to draw the culture medium from the first culture tank to the second culture tank when a signal from the second sensor is received.

4. A cell-cultivating device comprising:

a plurality of culture tanks having culture medium therein, wherein the plurality of culture tanks includes a first culture tank and a second culture tank;

a pipe connected between the plurality of culture tanks to permit communication between the plurality of culture tanks;

a peristaltic pump mounted on the pipe for forcing the culture medium to flow between the plurality of culture tanks so as to oscillate medium levels in the plurality of culture tanks;

a first sensor mounted near the top of the first culture tank;

a second sensor mounted near the top of the second culture tank; and a controller for receiving signals from the first and second sensors and actuating the peristaltic pump to draw the culture medium from the first culture tank to the second culture tank when a signal from the first sensor is received and actuating the peristaltic pump to draw the culture medium from the second culture tank to the first culture tank when a signal from the second sensor is received.

5. A cell-cultivating device comprising:

a plurality of culture tanks having culture medium therein;

a driving means for forcing the culture medium to flow between the plurality of culture tanks so as to oscillate medium levels in the plurality of culture tanks;

a buffer tank which is vertically moved by the driving means; and a plurality of pipes, wherein the plurality of pipes enables the buffer tank to communicate with the plurality of culture tanks.

6. A cell-cultivating device comprising:

a plurality of culture tanks having culture medium therein;

a driving means for forcing the culture medium to flow between the plurality of culture tanks so as to oscillate medium levels in a plurality of culture tanks, wherein the driving means is an oil pressure cylinder or an air pressure cylinder;

a buffer tank which is vertically moved by the driving means; and a plurality of pipes, wherein the plurality of pipes enables the buffer tank to communicate with the plurality of culture tanks.

7. A cell-cultivating device comprising:

a plurality of culture tanks having culture medium therein;

a communication means to permit communication between the culture tanks;

an air compressor for forcing gas into the culture tanks so as to vertically oscillate medium levels in the plurality of culture tanks;

sensors mounted near the tops of the plurality of culture tanks;

a first peristaltic pump;

a second peristaltic pump;

a first storage tank having a second culture medium therein, said second culture medium being continuously drawn from the first storage tank by the first peristaltic pump to the plurality of culture tanks;

a second storage tank; and a controller for receiving signals from the sensors and actuating the second peristaltic pump to draw culture medium from the plurality of culture tanks to the second tank by the second peristaltic pump.

8. A cell-cultivating device comprising:

a plurality of culture tanks having a culture medium therein, wherein the plurality of culture tanks includes a first culture tank and a second culture tank;

a communication means to permit communication between the plurality of culture tanks;

an air compressor for forcing gas into the plurality of culture tanks so as to vertically oscillate medium levels in the plurality of culture tanks;

a first sensor mounted near the top of the first culture tank;

a second sensor mounted near the bottom of the first culture tank; and a controller for receiving signals from the first and second sensors and actuating the air compressor so that gas is pushed into the first culture tank through a solenoid valve when a signal from the first sensor is received and actuating the air compressor so that gas is pushed into the second culture tank through a solenoid valve when a signal from the second sensor is received.

9. A cell-cultivating device comprising:

a plurality of culture tanks having culture medium therein, wherein the plurality of culture tanks includes a first culture tank and a second culture tank;

a communication means to permit communication between the plurality of culture tanks;

an air compressor for forcing gas into the plurality of culture tanks so as to vertically oscillate medium levels in the plurality of culture tanks;

a first sensor mounted near the bottom of the first culture tank;

a second sensor mounted near the bottom of the second culture tank; and a controller for receiving signals from the first and second sensors and actuating the air compressor so that gas is pushed into the second culture tank through a solenoid valve when a signal from the first sensor is received and actuating the air compressor so that gas is pushed into the first culture tank through a solenoid valve when a signal from the second sensor is received.

10. A cell-cultivating device comprising:

a plurality of culture tanks having culture medium therein, wherein the plurality of culture tanks includes a first culture tank and a second culture tank;

a communication means to permit communication between the culture tanks;

an air compressor that forces gas into the culture tanks so as to vertically oscillate medium levels in the plurality of culture tanks;

a first sensor mounted near the top of the first culture tank;

a second sensor mounted near the top of the second culture tank; and a controller for receiving signals from the first and second sensors and actuating the air compressor so that the gas is pushed into the first culture tank through a solenoid valve when a signal from the first sensor is received and actuating the air compressor so that gas is pushed into the second culture tank through a solenoid valve when a signal from the second sensor is received.

11. A cell-cultivating device comprising:

a plurality of culture tanks having culture medium and substrate means therein;

a communication means to permit communication between the culture tanks; and a driving means for forcing the culture medium to flow between the plurality of culture tanks so as to oscillate medium levels in the plurality of culture tanks, wherein said substrate means comprises carriers and wherein the carriers include woven carriers, nonwoven carriers, plates, porous carriers made of ceramics, porous carriers made of polymer and tissue engineering scaffolds including at least one plate having a handle at its edge and polymer films attached to the plate.

* * * * *